United States Patent
Hunter et al.

(10) Patent No.: US 10,481,104 B2
(45) Date of Patent: Nov. 19, 2019

(54) UTILIZING RESONANCE INSPECTION OF IN-SERVICE PARTS

(75) Inventors: Lemna J. Hunter, Corrales, NM (US); Leanne Jauriqui, Albuquerque, NM (US); Greg Weaver, Rio Rancho, NM (US)

(73) Assignee: Vibrant Corporation, Albuquerque, NM (US)

( * ) Notice: Subject to any disclaimer, the term of this patent is extended or adjusted under 35 U.S.C. 154(b) by 1029 days.

(21) Appl. No.: 13/278,380

(22) Filed: Oct. 21, 2011

(65) Prior Publication Data

US 2012/0158319 A1    Jun. 21, 2012

Related U.S. Application Data

(60) Provisional application No. 61/405,573, filed on Oct. 21, 2010.

(51) Int. Cl.
*G01N 22/00* (2006.01)
*G01N 29/46* (2006.01)
*G01N 29/44* (2006.01)
*G01N 29/34* (2006.01)
*G01N 29/04* (2006.01)
*G01N 29/12* (2006.01)

(52) U.S. Cl.
CPC ........... *G01N 22/00* (2013.01); *G01N 29/045* (2013.01); *G01N 29/12* (2013.01); *G01N 29/348* (2013.01); *G01N 29/4427* (2013.01); *G01N 29/4472* (2013.01); *G01N 29/46* (2013.01); *G01N 29/4409* (2013.01); *G01N 29/4445* (2013.01); *G01N 2291/103* (2013.01)

(58) Field of Classification Search
CPC ...... G01N 22/00; G01N 29/045; G01N 29/12; G01N 29/4409; G01N 29/4427; G01N 29/4445
See application file for complete search history.

(56) References Cited

U.S. PATENT DOCUMENTS

| | | | | | |
|---|---|---|---|---|---|
| 5,062,296 | A | * | 11/1991 | Migliori | 73/579 |
| 5,355,731 | A | * | 10/1994 | Dixon et al. | 73/579 |
| 5,408,880 | A | * | 4/1995 | Rhodes et al. | 73/579 |
| 5,425,272 | A | * | 6/1995 | Rhodes et al. | 73/579 |

(Continued)

FOREIGN PATENT DOCUMENTS

JP         06148148  A  *  5/1994  ............. G01N 29/20

OTHER PUBLICATIONS

Translation for JP 06148148.*

(Continued)

*Primary Examiner* — John C Kuan
(74) *Attorney, Agent, or Firm* — Holzer Patel Drennan

(57) ABSTRACT

Various embodiments relating to resonance inspections and in-service parts are disclosed. One protocol (150) includes conducting a resonance inspection of an in-service part (152). The frequency response of the in-service part may be compared with a resonance standard (154) for purposes of determining whether or not the in-service part is changing abnormally (156). An in-service part that is identified as changing abnormally may be characterized as being "rejected" (160). An in-service part that is no identified as changing abnormally may be characterized as being "accepted" (158).

12 Claims, 11 Drawing Sheets

(56) References Cited

U.S. PATENT DOCUMENTS

| | | | |
|---|---|---|---|
| 5,495,763 A * | 3/1996 | Rhodes et al. | 73/579 |
| 5,631,423 A * | 5/1997 | Rhodes | 73/579 |
| 5,641,905 A | 6/1997 | Schwarz et al. | |
| 5,837,896 A | 11/1998 | Rhodes et al. | |
| 5,886,263 A * | 3/1999 | Nath et al. | 73/579 |
| 5,952,576 A | 9/1999 | Schwarz | |
| 5,965,817 A | 10/1999 | Schwarz et al. | |
| 5,992,234 A | 11/1999 | Rhodes et al. | |
| 6,199,431 B1 * | 3/2001 | Nath et al. | 73/579 |
| 8,744,983 B2 * | 6/2014 | Miller | 706/12 |
| 2006/0271311 A1 * | 11/2006 | Gao et al. | 702/34 |
| 2007/0068605 A1 * | 3/2007 | Statnikov | 148/558 |
| 2008/0257047 A1 | 10/2008 | Pelecanos et al. | |
| 2009/0079424 A1 | 3/2009 | Tralshawala et al. | |
| 2010/0191107 A1 | 7/2010 | Bowers et al. | |
| 2011/0214496 A1 * | 9/2011 | Cahill | 73/121 |

OTHER PUBLICATIONS

Deneuville et al., "High frequency ultrasonic detection of C-crack defects in silicon nitride bearing balls" Ultrasonics 49 (2009) 89-93.*

Jhang, "Nonlinear Ultrasonic Techniques for Nondestructive Assessment of Micro Damage in Material: A Review" International Journal of Precision Engineering and Manufacturing vol. 10, No. 1, pp. 123-135 Jan. 2009.*

Oxford Advanced American Dictionary at OxfordLearnersDictionaries.com, retrieved on Nov. 17, 2015, available at http://www.oxfordlearnersdictionaries.com/definition/american_english/account-for.*

* cited by examiner

UTILIZING RESONANCE INSPECTION OF IN-SERVICE PARTS

CROSS-REFERENCE TO RELATED APPLICATIONS

This patent application is a conversion of, and claims priority to, U.S. Provisional Patent Application Ser. No. 61/405,573 that is entitled "UTILIZING RESONANCE INSPECTION OF IN-SERVICE PARTS," that was filed on Oct. 21, 2010, and the entire disclosure of which is hereby incorporated by reference in its entirety herein.

FIELD OF THE INVENTION

The present invention generally relates to the field of testing parts and, more particularly, to the field of resonance inspection of parts that involves exciting a part at a number of different frequencies and obtaining the frequency response of the part to the various excitations.

BACKGROUND OF THE INVENTION

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

The present invention is generally directed to resonance inspections. In at least certain instances, resonance inspection results from one in-service part are compared with resonance inspections results from one or more other in-service parts. Any resonance inspection-based comparison between one part and at least one other part for purposes of the present invention is directed to comparing parts that are at least functionally equivalent. "Functionally equivalent" includes where the parts are manufactured from common design specifications. However, "functionally equivalent" also encompasses the situation where parts are manufactured from different design specifications, but which may be used in the same end-use application. For instance, a given engine may allow turbine blades to be manufactured from either of a pair of design specifications. Resonance inspection-based comparisons for purposes of the present invention may be made between turbine blades used by the noted engine, but which are manufactured from the noted different design specifications. Typically, the differences between parts that are subject to a resonance inspection-based comparison for purposes of the present invention will not be of a radical nature (e.g., the parts will be on the same class (e.g., turbine blades), the parts will be very similar dimensionally).

A first aspect of the present invention is embodied by a method of evaluating in-service parts by resonance inspection. A resonance inspection includes exciting a given part at a plurality of input frequencies and obtaining a frequency response of the part. A resonance inspection is performed on a first in-service part for purposes of the first aspect. The frequency response from the resonance inspection of the first in-service part is compared with what may be characterized as a "resonance standard." Generally, this resonance standard defines how the first in-service part should normally change while in service. The comparison of the frequency response from the resonance inspection of the first in-service part to the resonance standard is utilized to determine if the first in-service part is changing abnormally.

A number of feature refinements and additional features are applicable to the first aspect of the present invention. These feature refinements and additional features may be used individually or in any combination. The following discussion is applicable to the first aspect, up to the start of the discussion of a second aspect of the present invention.

The resonance standard, against which the frequency response from the resonance inspection of the first in-service part is compared, may be stored on a computer-readable storage medium. For instance, the resonance standard may be stored on a hard drive, disk drive, optical drive, flash drive, or the like, that is utilized by a computer that may be utilized to make the comparison required by the first aspect. In any case, the comparison of the frequency response from the resonance inspection of the first in-service part with the resonance standard, as well as the determination as to whether or not the first in-service part is changing abnormally, may utilize at least one processor (e.g., one or more processors of any appropriate type, where multiple processors may be integrated/implemented in any appropriate manner).

The resonance standard, against which the frequency response from the resonance inspection of the first in-service part is compared, may be of any appropriate type and/or defined in any appropriate manner. One embodiment has this resonance standard including spectra (e.g., a "snapshot" of the frequency response of a part at one or more points in time) of at least one other in-service part (e.g., an in-service part other than the first in-service part). Another embodiment has this resonance standard being in the form of a mathematical model (e.g., resonance inspection results generated from software based upon projections/predictions as to how a part should normally change over time when in use or service).

The resonance standard associated with the first aspect may be directed to comparing how the first in-service part is changing relative to a population of in-service parts (e.g., in-service parts that are comparable with the first in-service part in one or more respects, including where the in-service parts within the population and the first in-service part are produced from or in accordance with common specifications). If the first in-service part is changing at least generally in accordance with the population, the first in-service part may be characterized as changing normally. Otherwise, the first in-service part may be characterized as changing abnormally.

The resonance standard used by the first aspect may be based upon resonance inspection data from a population of in-service parts. In one embodiment, the population of in-service parts does not include the first in-service part. In any case, the resonance standard may be in the form of one or more representative spectra (e.g., one spectra for each of a plurality of in-service parts that are part of the population). A given representative spectra may also be in the form of an average of spectra from each of the plurality of in-service parts that are included within the noted population (or from a plurality of in-service parts within the population). The resonance standard may also be in the form of spectra from a single member of the population.

Consider the case where a first assembly is defined by what may be characterized as first assembly specifications. This first assembly may include a first part. Although this first part could be required to conform with one set of first part specifications for purposes of complying with the overall first assembly specifications (e.g., where the first in-service part and the population of in-service parts are defined by and/or manufactured in accordance with common specifications), it may be such that first assembly specifications allows this first part to conform with any one of a plurality of different first part specifications (e.g., the first assembly specifications could allow the first part to be in accordance with either specifications #1 or specifications #2, where there is at least one difference between specifications #1 and #2). As such, it may be that the first in-service part is interchangeable (e.g., functionally) with the in-service parts in the population, but may actually vary in one or more respects from one or more in-service parts in the population.

The resonance standard is subject to yet another characterization. A plurality of first parts may be manufactured. Each of these first parts may be put into service (e.g., used for the intended purpose and/or in an intended end-use application; after being released from production for use by a customer, end user, or the like). The first in-service part associated with the first aspect may be one of these first parts. After the plurality of first parts have been in service for a certain duration (e.g., measured in any appropriate manner, such as cycles of operation, operating time, a certain time period, or the like), a resonance inspection is performed on each of a plurality of the first parts. The resonance standard may be defined by the results of the resonance inspection of at least some of the plurality of first parts, including where the resonance standard is defined by the results of the resonance inspection of one or more of the plurality of first parts other than the first in-service part.

The resonance standard used by the first aspect may include results from a plurality of spaced-in-time resonance inspections that were previously performed on another in-service part that corresponds with the first in-service part. "Corresponding with" includes where this second in-service part and first in-service part each conform to predetermined specifications. It should be appreciated that these "predetermined specifications" may in fact allow the second in-service part and the first in-service part to vary in one or more respects, other than according to a specified tolerance (e.g., the first and second in-service part may be interchangeable for an end-use application, but they may differ in one or more respects and other than by having a different value within a specified tolerance). In any case and in one embodiment, this "second" in-service part is incorporated by what may be characterized as a "fleet leader." A "fleet leader" may be an end use of the second in-service part that experiences higher-than-normal usage over a certain period of time (e.g., an aircraft that has a higher-than-average number of landings over a certain period of time). In another embodiment, this "second" in-service part is one that has undergone accelerated life testing. "Accelerated life testing" may be characterized as involving the acceleration of failures of a part for the purpose of quantifying the life characteristics of the part at normal use conditions.

"Usage information" (any parameter that characterizes the amount of usage of a given in-service part, such as hours of operation, cycles of operation, or the like) may or may not be utilized for purposes of determining whether the first in-service part is changing normally or abnormally in the case of the first aspect. For instance, the first aspect may be configured so that the first in-service part is characterized as changing normally, even though the resonance inspection results of the first in-service part comply with the resonance standard at different numbers of cycles. That is, the first aspect may be configured to characterize the first in-service part as changing normally if its resonance inspection results at the 5,000 cycle level comply with the resonance standard at the 10,000 cycle level.

The first aspect may be also configured so that the frequency response from at least one resonance inspection of the first in-service part (e.g., the first resonance inspection that is undertaken after the first in-service part has been put into service) must comply with a corresponding part of the resonance standard in terms of amount of usage. For instance, the resonance inspection data from a resonance inspection of the first in-service part at 5,000 cycles may be required to comply with the resonance inspection data from the resonance standard that is also associated with 5,000 cycles). Thereafter, the first aspect may be configured so that the first in-service part is characterized as changing normally, even though the resonance inspection results of the first in-service part comply with the resonance standard at different numbers of cycles. That is, the first aspect may be configured to characterize the first in-service part as changing normally if its resonance inspection data at 10,000 cycles complies with the resonance standard at 15,000 cycles.

Another option is for the first aspect to be configured so that the frequency response from at least one resonance inspection of the first in-service part (e.g., the first resonance inspection that is undertaken after the first in-service part has been put into service) must at all times comply with a corresponding part of the resonance standard in terms of amount of usage. For instance, the resonance inspection data from a resonance inspection of the first in-service part at 5,000 cycles may be required to comply with the resonance inspection data from the resonance standard that is also associated with 5,000 cycles, the resonance inspection data from a resonance inspection of the first in-service part at 10,000 cycles may be required to comply with the resonance inspection data from the resonance standard that is also associated with 10,000 cycles, and so forth. Yet another option is for the first aspect to be configured so as to not utilize any usage information for purposes of determining whether the first in-service part is changing normally (e.g., so long as the resonance inspection data on the first in-service part complies with any resonance inspection data of the resonance standard, the first in-service part may be characterized as changing normally for purposes of the first aspect).

A second aspect of the present invention is embodied by a method of evaluating in-service parts by resonance inspection. A resonance inspection includes exciting a given part at a plurality of input frequencies and obtaining a frequency response of the part. For purposes of the second aspect, a resonance inspection is performed on a plurality of in-service parts that collectively define what may be characterized as a first part group. A first subset is selected from the first part group and is characterized or associated with being "normal." Results from the resonance inspection of at least one in-service part from the first subset may be used to define a normal standard. A second subset is selected from the first part group and is characterized or associated with being "abnormal." Results from the resonance inspection of at least one in-service part from the second subset may be used to define an abnormal standard. Both the normal and abnormal standards may be stored on a computer-readable storage medium of what may be characterized as a resonance inspection tool or system.

A number of feature refinements and additional features are applicable to the second aspect of the present invention. These feature refinements and additional features may be used individually or in any combination. The following discussion is applicable to the second aspect, up to the start of the discussion of a third aspect of the present invention. Initially, the second aspect may be repeated any appropriate number of times (e.g., for a number of different first part groups; at a number of different points in time in relation to the same first part group). The resonance inspection tool may include multiple normal standards, multiple abnormal standards or both. The normal standard may include resonance inspection results from one or more resonance inspections of one or more in-service parts from any first subset of any first part group, the abnormal standard may include resonance inspection results from one or more resonance inspections of one or more in-service parts from any second subset of any first part group, or both.

The selection that defines the first subset (e.g., "normal") may be based upon data other than results of the resonance inspection of each of the plurality of in-service parts from which the first subset is defined. In one embodiment, the selection for purposes of defining the first subset utilizes nondestructive testing, destructive testing, or both. Similarly, the selection that defines the second subset (e.g., "abnormal") may be based upon data other than results of the resonance inspection of each of the plurality of in-service parts from which the second subset is defined. In one embodiment, the selection for purposes of defining the second subset utilizes nondestructive testing, destructive testing, or both. One or more nondestructive testing techniques may be used, one or more destructive techniques may be used, or both, in relation to the second aspect. Representative nondestructive testing techniques that may be used in relation to the second aspect includes without limitation visual inspection, microscopy, magnetic particle, penetrant, eddy current, x-ray, computed tomography, flash thermography, ultrasound, sonic infra-red, phased array, or the like. Representative destructive testing techniques that may be used in relation to the second aspect includes without limitation fatigue testing, static testing, thermal testing, metalography, sectioning, ablation, chemical reduction, or the like.

Using the results of the resonance inspection to define a normal standard for purposes of the second aspect may entail defining at least one relationship (e.g., a first relationship) in the spectra provided by the resonance inspection of at least one in-service part that is within the first subset. Another embodiment is directed to using the results of the resonance inspection to define a normal standard for purposes of the second aspect, and more specifically defining at least one relationship in the spectra provided by the resonance inspection of a plurality of in-service parts that are each within the first subset. Similarly, using the results of the resonance inspection to define an abnormal standard for purposes of the second aspect may entail defining at least one relationship (e.g., a second relationship) in the spectra provided by the resonance inspection of at least one in-service part that is within the second subset. Another embodiment is directed to using the results of the resonance inspection to define an abnormal standard for purposes of the second aspect, and more specifically defining at least one relationship in the spectra provided by the resonance inspection of a plurality of in-service parts that are each within the second subset.

The resonance inspection tool or system may be used to assess an in-service part after the normal and abnormal standards have been stored in relation to the second aspect. The normal and abnormal standards associated with the second aspect may be characterized as collectively defining a "sort functionality" for the resonance inspection tool or system. Such a "sort functionality" may be directed to providing the resonance inspection tool or system with the ability to determine whether an in-service part should be accepted or rejected after a resonance inspection has been conducted using the resonance inspection tool or system (along with the normal and/or abnormal standards).

Consider the case where a resonance inspection of a first in-service part is conducted using the resonance inspection tool having the stored normal and abnormal standards from the second aspect. The results from this particular resonance inspection may be compared with at least one of the normal standard and the abnormal standard. In one embodiment, the first in-service part is accepted by the resonance inspection tool if the results of its resonance inspection comply with the normal standard. In one embodiment, the first in-service part is rejected by the resonance inspection tool if the results of its resonance inspection fail to comply with the normal standard. In yet another embodiment, the first in-service part is rejected by the resonance inspection tool if the results of its resonance inspection comply with the abnormal standard. An in-service part could be rejected by the resonance inspection tool if the results of the corresponding resonance inspection fails to comply with the normal standard, complies with the abnormal standard, or both.

The normal standard, the abnormal standard, or both, may include resonance inspection data from the resonance inspection of one or more in-service parts. For instance, the normal standard could be a collection of a plurality of spectra (from a resonance inspection) for in-service parts that have been characterized as "normal," the abnormal standard could be a collection of a plurality of spectra (from a resonance inspection) for in-service parts that have been characterized as "abnormal." The "usage information" discussed above in relation to the first aspect could be utilized by this second aspect as well. As such, the normal standard could include at least one spectra (from a resonance inspection) for an in-service part that has been characterized as normal, and corresponding usage information may be stored in relation to each such spectra (e.g., the normal standard could include spectra for a in-service part at 5,000 cycles, 10,000 cycles, 15,000 cycles, and so forth). Similarly, the abnormal standard could include at least one spectra (from a resonance inspection) for an in-service part that has been characterized as abnormal, and corresponding usage information may be stored in relation to each such spectra (e.g., the normal standard could include spectra for an in-service part at 5,000 cycles, 10,000 cycles, 15,000 cycles, and so forth).

A third aspect of the present invention is embodied by a method of evaluating new production parts by resonance inspection. A resonance inspection includes exciting a given part at a plurality of input frequencies and obtaining a frequency response of the part. For purposes of the third aspect, a resonance inspection is performed on a first in-service part. A first manufacturing defect is identified in the first in-service part. Data from the resonance inspection of the first in-service part is selected and where this resonance inspection data corresponds with the first manufacturing defect (e.g., the selected resonance inspection data correlates with the first manufacturing defect). A new production part sort functionality of a resonance inspection tool is updated based upon this selection of data from the noted resonance inspection.

A number of feature refinements and additional features are applicable to the third aspect of the present invention. These feature refinements and additional features may be used individually or in any combination. The following discussion is applicable to the third aspect, up to the start of the discussion of a fourth aspect of the present invention. Generally, the third aspect may be characterized as using the results of a resonance inspection of an in-service part to adjust the sort functionality used by a resonance inspection tool to assess new production parts. In one embodiment: 1) prior to being updated in accordance with the third aspect, the new production part sort functionality of the resonance inspection tool was configured to actually accept a new production part that has the first manufacturing defect; and 2) after being updated in accordance with the third aspect, the new production part sort functionality of the resonance inspection tool should be of a configuration that will reject a new production part that has the first manufacturing defect.

The first manufacturing defect in the first in-service part may become more evident as the first in-service part is put into service. Data from one or more resonance inspections of the first in-service part (including when the same was in the form of a new production part—prior to being released from production and/or put into service by a customer, end user, or the like) may be analyzed to determine how the new production part sort functionality of the resonance inspection tool should be adapted so as to be able to identify the existence of the first manufacturing defect in a new production part. The resonance inspection tool may then be configured to reject a new production part having such a first manufacturing defect.

The first manufacturing defect in the first in-service part may be identified in any appropriate manner. In one embodiment, nondestructive testing, destructive testing, or both may be used to originally identify the first manufacturing defect. One or more nondestructive testing techniques may be used, one or more destructive techniques may be used, or both, in relation to the third aspect. Those representative nondestructive and destructive testing techniques discussed above in relation to the second aspect may be used by the third aspect as well. In any case and in one embodiment, after the first manufacturing defect has been identified, resonance inspection results may be reviewed to identify how the first manufacturing defect may be identified from the resonance inspection results.

A fourth aspect of the present invention is embodied by a method of evaluating in-service parts by resonance inspection. A resonance inspection includes exciting a given part at a plurality of input frequencies and obtaining a frequency response of the part. A resonance inspection is performed on a first in-service part at a plurality of different times in its lifecycle (e.g., throughout the life of the first in-service part). First resonance inspection data is monitored for an occurrence of a first condition. This first condition is a predetermined time-rate-of-change in the first resonance inspection data over multiple resonance inspections. An end-of-life determination for the first in-service part is based upon the identification of an occurrence of the first condition.

A number of feature refinements and additional features are applicable to the fourth aspect of the present invention. These feature refinements and additional features may be used individually or in any combination. The following discussion is applicable to at least the fourth aspect. Generally, the fourth aspect may be characterized as being directed to basing an end-of-life determination on a certain time-rate-of-change in at least part of the resonance inspection data from multiple and spaced in time resonance inspections of the first in-service part (e.g., resonance inspections conducted on the first in-service part at 5,000 cycles, 10,000 cycles, 15,000 cycles, and so forth).

The first in-service part may undergo resonance inspections on any appropriate basis for purposes of the fourth aspect. For instance, a resonance inspection of the first in-service part may be conducted on a scheduled basis and based upon some type of usage information (e.g., hours of operation; cycles of operation). For instance, the first in-service part could be scheduled for a resonance inspection ever "x" cycles. The first in-service part could also be scheduled for a resonance inspection on what may be characterized as a "target cycle" basis. Each target cycle could be a range of cycles, a minimum number of cycles, or the like. A resonance inspection could be recommended for the first in-service part when it has been operated for 4,000-6,000 cycles, another resonance inspection could be recommended for the first in-service part when it has been operated for 9,000-11,000 cycles, and so forth. A resonance inspection could be recommended for the first in-service part when it has been operated for at least 5,000 cycles, another resonance inspection could be recommended for the first in-service part when it has been operated for at least 10,000 cycles, and so forth.

The first resonance inspection data used by the fourth aspect may be stored on a computer-readable storage medium. In one embodiment, the monitoring of the first resonance inspection data is performed by a computer. A resonance inspection tool may monitor the first resonance inspection data for an occurrence of a first condition.

The resonance inspection data that is acquired on the first in-service part may include the first resonance inspection data. In one embodiment, the first resonance inspection data is only part of the resonance inspection data that is acquired from each resonance inspection of the first in-service part. The first resonance inspection data may also be characterized as being based upon and/or derived from the resonance inspection data acquired from each resonance inspection of the first in-service part.

The first resonance inspection data may be in the form of a frequency shift in the resonance inspection data acquired from multiple resonance inspections of the first in-service part. The first resonance inspection data may be in the form of: 1) a relative shift of at least one peak in the resonance inspection data acquired from multiple resonance inspections of the first in-service part (e.g., a shift of a first peak in the resonance inspection data relative to a second peak in the resonance inspection data); 2) an absolute shift of at least one peak in the resonance inspection data acquired from multiple resonance inspections of the first in-service part (e.g., a shift of a first peak in the resonance inspection data); 3) an appearance of at least one peak in the resonance inspection data acquired from multiple resonance inspections of the first in-service part; and 4) a disappearance of at least one peak in the resonance inspection data acquired from multiple resonance inspections of the first in-service part.

The first resonance inspection data may be plotted. The predetermined time-rate-of-change associated with the fourth aspect may be in the form of a predetermined slope (e.g., rise over run) for the plot. Therefore, the first condition may occur when the noted plot exhibits at least a certain slope. In one embodiment, the noted plot is of a frequency shift (e.g., how a certain peak in resonance inspection data for the first in-service parts shifts over time), where the y-axis may characterize this shift in any appropriate manner (e.g., expressed as a percentage change in the location of a peak from a previous-in-time resonance inspection), and where the x-axis may characterize corresponding usage information in any appropriate manner (e.g., number of cycles). Consider the case where Peak 1 is at a certain frequency at time to (e.g., when released from production). Peak 1 may be at a different frequency at time $t_1$ (e.g., at the time of the first resonance inspection), at yet a different frequency at time $t_2$ (e.g., at the time of the second resonance inspection), and so forth. How Peak 1 is shifting may be quantified by the y-axis of the noted plot and for the associated time (where "time" may be expressed in any appropriate manner, such as in hours, cycles, or the like).

A number of feature refinements and additional features are separately applicable to each of above-noted first, second, third, and fourth aspects of the present invention. These feature refinements and additional features may be used individually or in any combination in relation to each of the above-noted first, second, third, and fourth aspects. An "in-service part" in the context of the present invention encompasses a part that has been used to at least some extent after having been released by the manufacturer. An in-service part may be a part that has been put into use by a party other than the manufacturer (e.g., a customer or end user). Although an in-service part could be used autonomously, an in-service part may be incorporated by a larger assembly (e.g., a turbine blade in a jet engine).

A resonance inspection of a given part may utilize a first transducer that excites or drives the part at multiple frequencies (e.g., by sweeping through a predetermined range of frequencies), along with at least one other transducer that measures the frequency response of this part to such excitations or drive frequencies (e.g., thereby encompassing using two "receiver" transducers). Any number of frequencies may be used to excite the part for the resonance inspection, and the excitation frequencies may be input to the part in any appropriate pattern and for any appropriate duration. Another option is to use a single transducer for performing a resonance inspection. In this case, a transducer may drive a given part at a certain frequency for a certain amount of time, and thereafter this same transducer may be used to obtain the frequency response of this part (e.g., after terminating the driving of the transducer at an input frequency). This may be repeated for multiple input or drive frequencies.

Any appropriate combination of excitation or drive frequencies may be used for a resonance inspection for purposes of the present invention. Each transducer that is used to perform a resonance inspection for purposes of the present invention may be of any appropriate size, shape, configuration, and/or type, and will typically be in contact with the part (including where one or more transducers support the part to at least some extent). Although a resonance inspection for purposes of the present invention could be performed in situ (e.g., with the part in an installed condition or state, for instance on a turbine blade that is mounted within a jet engine), such a resonance inspection could be performed on a part that has been removed from service (e.g., at a time when the part is in an uninstalled condition or state, for instance on a turbine blade that has been removed from a jet engine).

The various aspects of the present invention each may be implemented as a method and/or as an inspection system or tool. In the case of an inspection system or tool, an assessment module may be configured to execute the assessments noted herein (e.g., such an assessment module may utilized logic that is configured to assess a particular part in accordance with a defined protocol), where a given part may be excited and the frequency response may be obtained in accordance with any one or more of the configurations addressed herein.

Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system utilizes "a frequency response transducer" alone does not mean that the resonance inspection system utilizes only a single frequency response transducer). Moreover, any failure to use phrases such as "at least one" also does not limit the corresponding feature to the singular (e.g., indicating that a resonance inspection system utilizes "a frequency response transducer" alone does not mean that the resonance inspection system utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
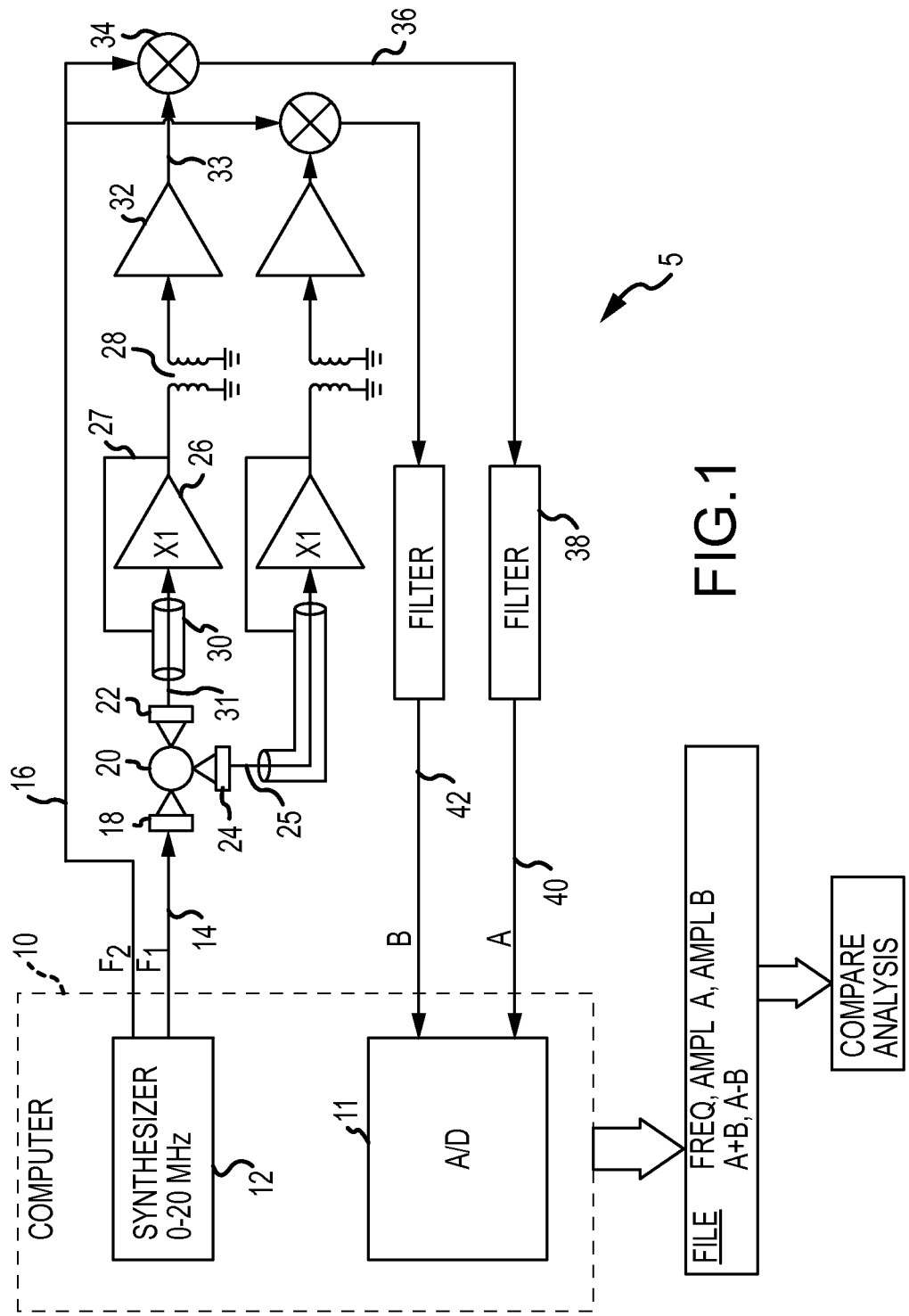
FIG. 1 is a block-diagram of one embodiment of a resonance inspection tool.
Figure 2:
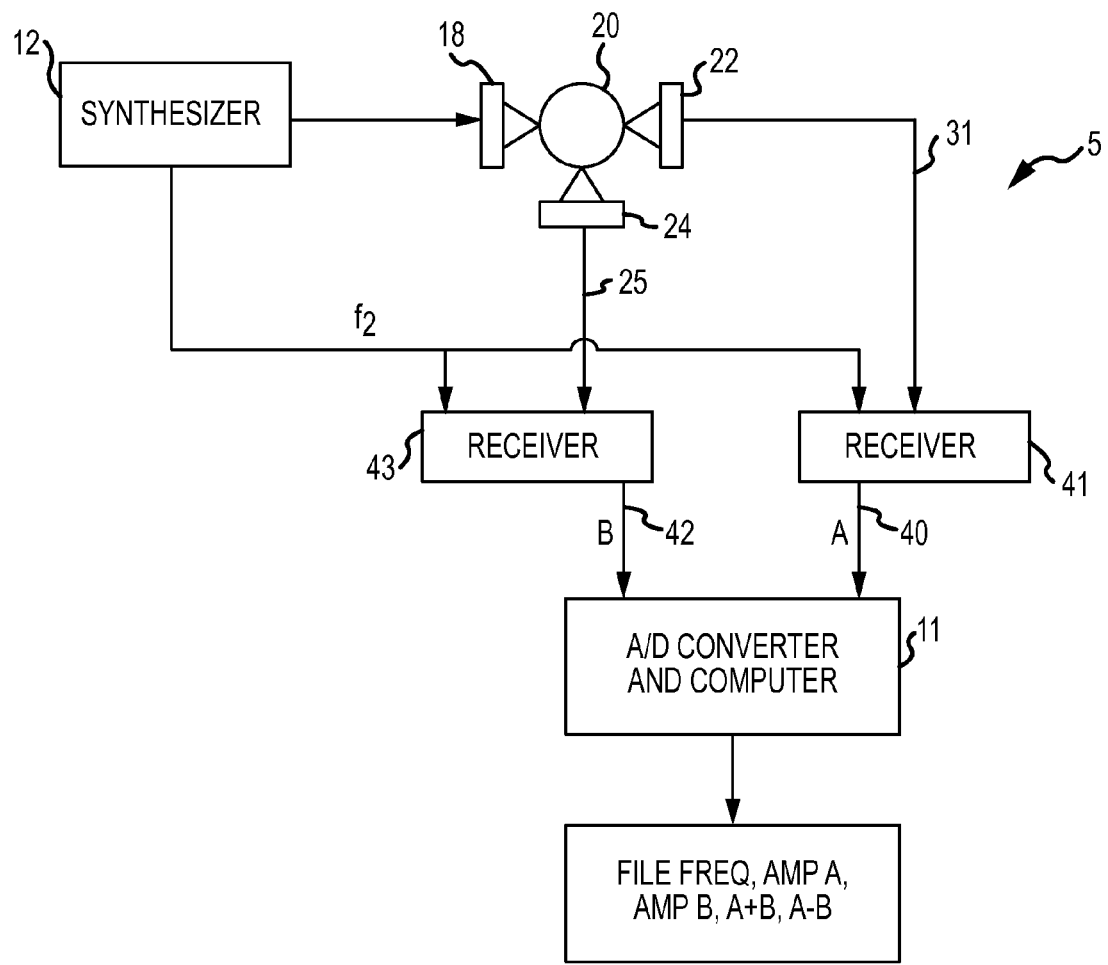
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and A/D converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is a provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present. Once information is entered into file, subsequent processing can be used to generate a signature or characterize the object 20 such as the resonant magnitudes, the sum of resonant magnitudes, the difference resonant magnitudes, or other manipulations of the multiple channel multiple frequency measurement which is used to perform the unique signature of the object 20. The magnitude of the outputs at each sensor location for each resonance frequency may be compared.

Figure 3:
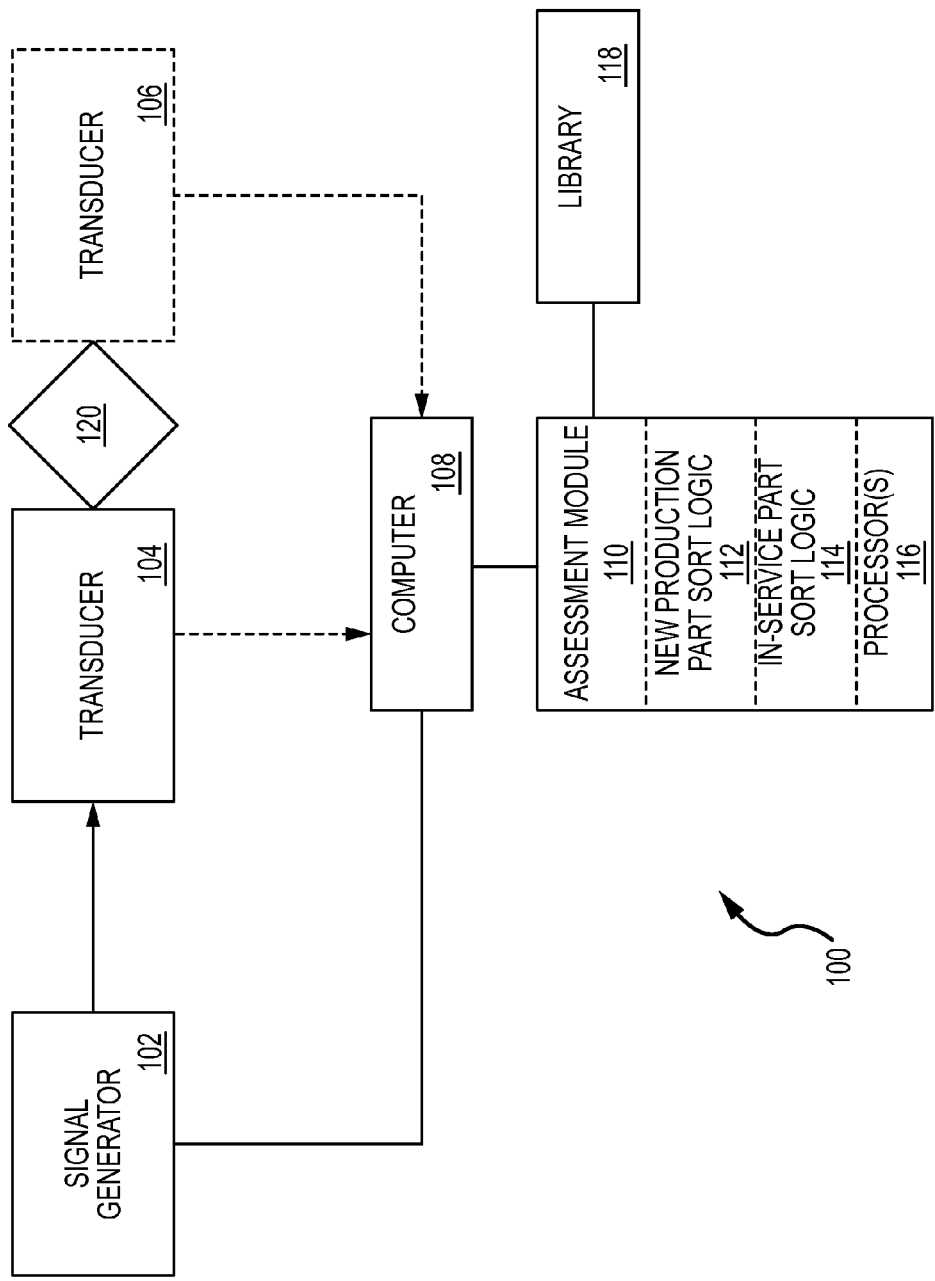
FIG. 3 is a block-diagram of another embodiment of a resonance inspection tool.

Another embodiment of a resonance inspection tool or system is illustrated in FIG. 3 and is identified by reference numeral 100. The resonance inspection tool 100 includes a signal generator 102 of any appropriate type, at least one transducer of any appropriate type that interfaces with a part 120 (e.g. via physical contact) that is to undergo a resonance inspection (e.g., transducer 104), and a computer 108. The computer 108 may include what may be characterized as an assessment module 110. Generally, the assessment module 110 may be configured to evaluate the results of a resonance inspection, for instance for purposes of determining whether the part 120 should be accepted or rejected by the resonance inspection tool 100, determining whether the part 120 is at an end-of-life state or condition, or the like. A part 120 that is "accepted" by the resonance inspection tool 100 may mean that the resonance inspection tool 100 has determined that the part 120 may be put into service (e.g., utilized for its intended purpose(s) and/or used according to its design specifications). In one embodiment, a part 120 that has been accepted by the resonance inspection tool 100 means that the tool 100 has determined that the part 120 is free of defects, is not in an end-of-life condition or state, is aging normally, or any combination thereof. A part 120 that is "rejected" by the resonance inspection tool 100 may mean that the resonance inspection tool 100 has determined that the part 120 should not be put into service (e.g., should not be utilized for its intended purpose(s) and/or should no longer be used according to its design specifications). In one embodiment, a part 120 that has been rejected by the resonance inspection tool 100 means that the tool 100 has determined that the part 120 includes at least one defect, is at or near an end-of-life condition or state, is aging abnormally, or any combination thereof.

A part 120 that is analyzed or assessed by the resonance inspection tool 100 may be of any appropriate size, shape, configuration, type, and/or class. For purposes of the resonance inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part may be incorporated by an assembly or system (e.g., a turbine blade (an in-service part) in a jet engine (an assembly or system)).

The signal generator 102 generates signals that are directed to the transducer 104 for transmission to the part 120 in any appropriate manner/fashion (e.g., via physical contact between the transducer 104 and the part 120). Signals provided by the signal generator 102 are used to mechanically excite the part 120 (e.g., to provide energy to the part 120 for purposes of inducing vibration). Multiple frequencies may be input to the part 120 through the transducer 104 in any appropriate manner. This may be characterized as "sweeping" through a range of frequencies that are each input to the part 120, and this may be done in any appropriate manner for purposes of the resonance inspection tool 100. Any appropriate number/range of frequencies may be utilized, and any appropriate way of progressing through a plurality of frequencies (e.g., a frequency range) may be utilized by the resonance inspection tool 100.

In one embodiment, at least one other transducer 106 is utilized in the resonance inspection of the part 120 using the resonance inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the part 120. It may be such that the part 120 is in fact entirely supported by the transducer 104 and any additional transducers 106. Each transducer 106 that is utilized by the resonance inspection tool 100 is used to acquire the frequency response of the part 120 to the frequencies input to the part 120 by the drive transducer 104, and therefore each transducer 106 may be characterized as an output or receiver transducer 106.

Another embodiment of the resonance inspection tool 100 of FIG. 3 utilizes only the transducer 104. That is, no additional transducers 106 are utilized by the resonance inspection tool 100 in this case, and therefore the transducer 106 is presented by dashed lines in FIG. 3. In this case, the transducer 104 is used to input a drive signal to the part 120 (e.g., to excite the part 120 at a plurality of different frequencies), and is also used to acquire the frequency response of the part 120 to these input drive frequencies. For instance, a first drive signal at a first frequency (from the signal generator 102) may be transmitted to the part 120 through the transducer 104, the transmission of this first drive signal may be terminated, and the transducer 104 may be used to acquire a first frequency response of the part 120 to this first drive signal (including while a drive signal is being transmitted to the part 120). The signal generator 102 may also be used provide a second drive signal at a second frequency to the transducer 104, which in turn transmits the second drive signal to the part 120, the transmission of this second drive signal may be terminated, and the transducer 104 may once again be used to acquire a second frequency response of the part 120 to this second drive signal (including while a drive signal is being transmitted to the part 120). This may be repeated any appropriate number of times and utilizing any appropriate number of frequencies and frequency values. One or more drive signals may be sequentially transmitted to the part 120 by the signal generator 102 and transducer 104, one or more drive signals may be simultaneously transmitted to the part 120 by the signal generator 102 and transducer 104, or any combination thereof.

The frequency response of the part 120 is transmitted to the computer 108 of the resonance inspection tool 100 of FIG. 3. This computer 108 may be of any appropriate type and/or configuration, and is used by the resonance inspection tool 100 to evaluate the part 120 in at least some fashion (e.g., to determine whether to accept or reject the part 120). Generally, the part 120 is vibrated by the transducer 104 according to a predetermined signal(s), and the part 120 is evaluated by the resulting vibrational response of the part 120. For instance, this evaluation may entail assessing the part 120 for one or more defects of various types, assessing whether the part 120 is at or near the end of its useful, life, assessing whether the part 120 is aging normally or abnormally, or any combination thereof.

The computer 108 may incorporate and utilize the above-noted assessment module 110 to evaluate the response of the part 120 to a resonance inspection. The assessment module 110 may be of any appropriate configuration and may be implemented in any appropriate manner. In one embodiment, the assessment module 110 includes at least one new production part sort logic 112 (e.g., logic configured to determine whether to accept or reject new production parts), at least one in-service part sort logic 114 (e.g., logic configured to determine whether to accept or reject in-service parts), along with one or more processors 116 of any appropriate type and which may be implemented in any appropriate manner. The assessment of the response of the part 120 to the input drive signals may entail comparing the response to a library 118 utilized by the resonance inspection tool 100. This library 118 may be stored on a computer-readable storage medium of any appropriate type or types, including without limitation by using one or more data storage devices of any appropriate type and disposed in any appropriate arrangement.

Figure 4:
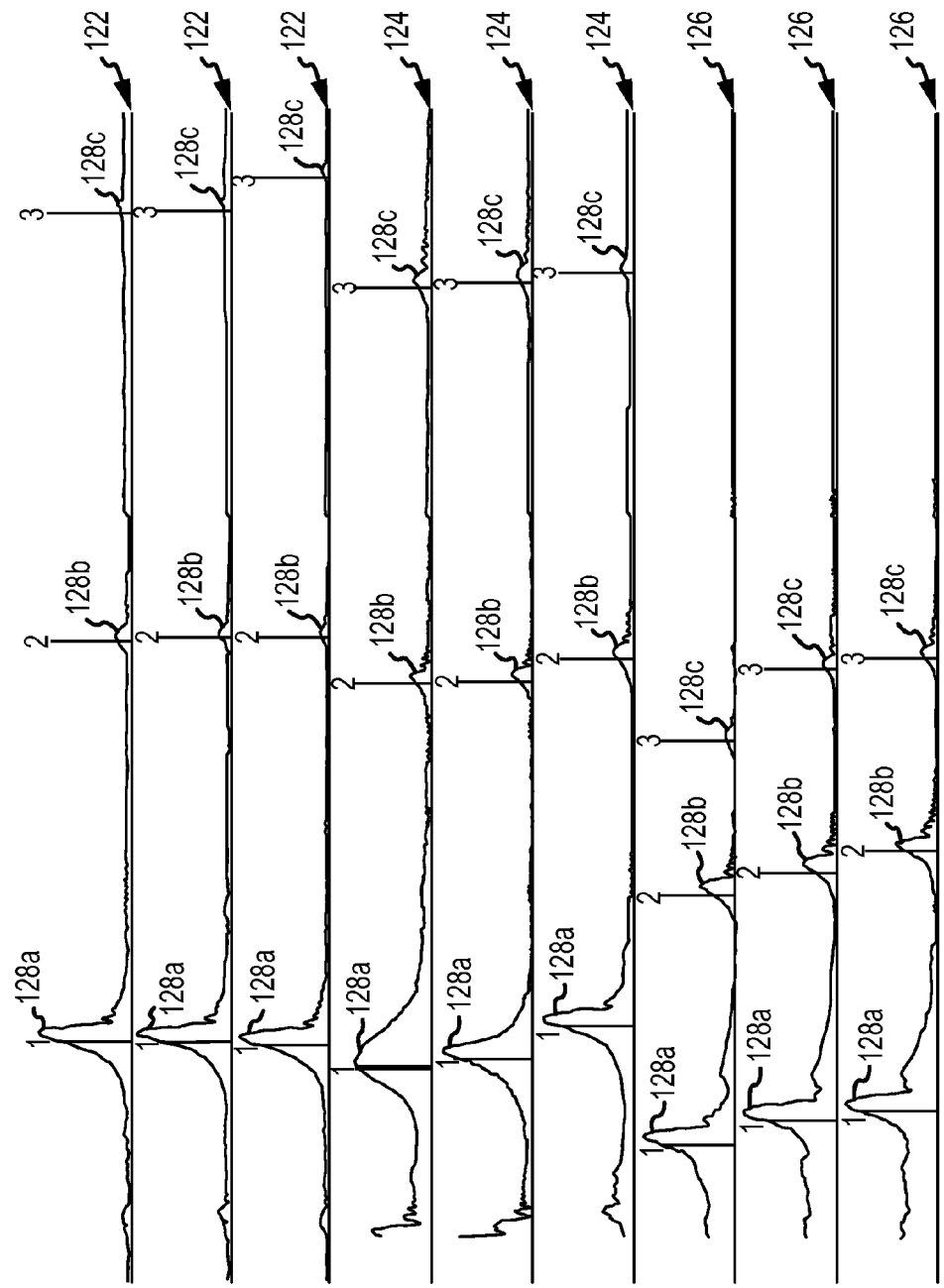
FIG. 4 presents various resonance inspection results of parts that may be included in the library utilized by the resonance inspection tool of FIG. 3.

The library 118 of the resonance inspection tool 100 may include various types of resonance inspection results to allow the resonance inspection tool 100 to assess a part 120. Generally, the resonance inspection results from the part 120 are compared with data in the library 118 from at least one other part that is the same as the part 120 in one or more respects (e.g., a part 120 in the form of a turbine blade will be compared to turbine blade data in the library 118; a part 120 in the form of a ball bearing will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the resonance inspection tool 100. Note how the three peaks 128a, 128b, and 128c differ in at least one respect between the various spectra 122, but yet the corresponding new production part 120 is acceptable in all three instances.

The three spectra 124 shown in FIG. 4 represent the frequency response of an in-service production part 120 to a certain input frequency, and where this in-service part 120 has been accepted by the resonance inspection tool 100. Note how the three peaks 128a, 128b, and 128c in the spectra 124 differ in at least one respect from the corresponding peaks 128a, 128b, and 128c in the spectra 122 (again, associated with a new production part 120).

The three spectra 126 shown in FIG. 4 represent the frequency response of an in-service production part 120 to a certain input frequency, and where this in-service part 120 has been rejected by the resonance inspection tool 100. Note how the three peaks 128a, 128b, and 128c in the spectra 126 differ in at least one respect from the corresponding peaks 128a, 128b, and 128c in the spectra 124 (again, associated with an in-service part 120 that the resonance inspection tool 100 would accept). Generally, each of the peaks 128a, 128b, and 128c in the spectra 126 has shifted to the left compared to the corresponding peaks 128a, 128b, and 128c in the spectra 122 and 124. Moreover, note the "compression" between the peaks 128a, 128b in the spectra 126 compared to the spectra 122, 124, as well as the "compression" between the peaks 128b, 128c in the spectra 126 compared to the spectra 122, 124.

Figure 5:
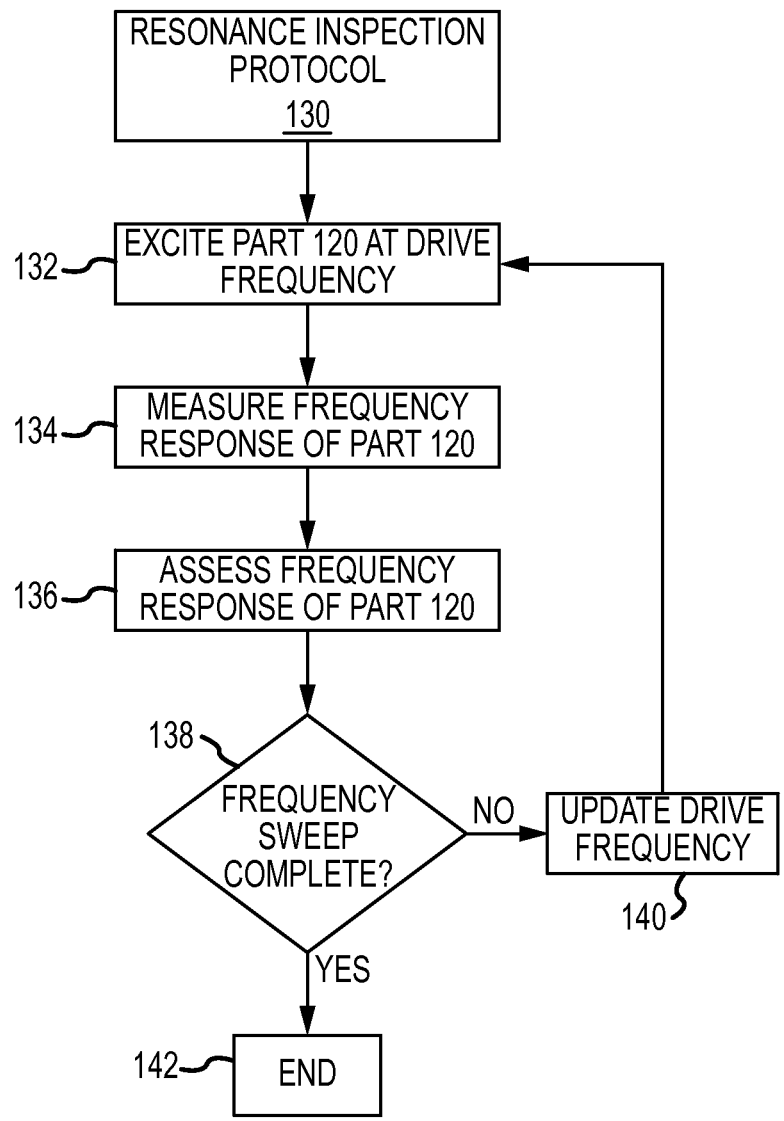
FIG. 5 is one embodiment of a resonance inspection protocol that may be utilized by a resonance inspection tool.

One embodiment of a resonance inspection protocol that may be utilized by the resonance inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 for repetition in accordance with the foregoing. Once the part 120 has been driven at each of the desired frequencies, the protocol 130 is terminated pursuant to step 142.

Step 136 of the resonance inspection protocol 130 is again directed to assessing the response (e.g., frequency) of the part 120 (e.g., using the sort logic 112 or 114 and/or comparing the response of the part 120 to the library 118 of the resonance inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

Figure 6:
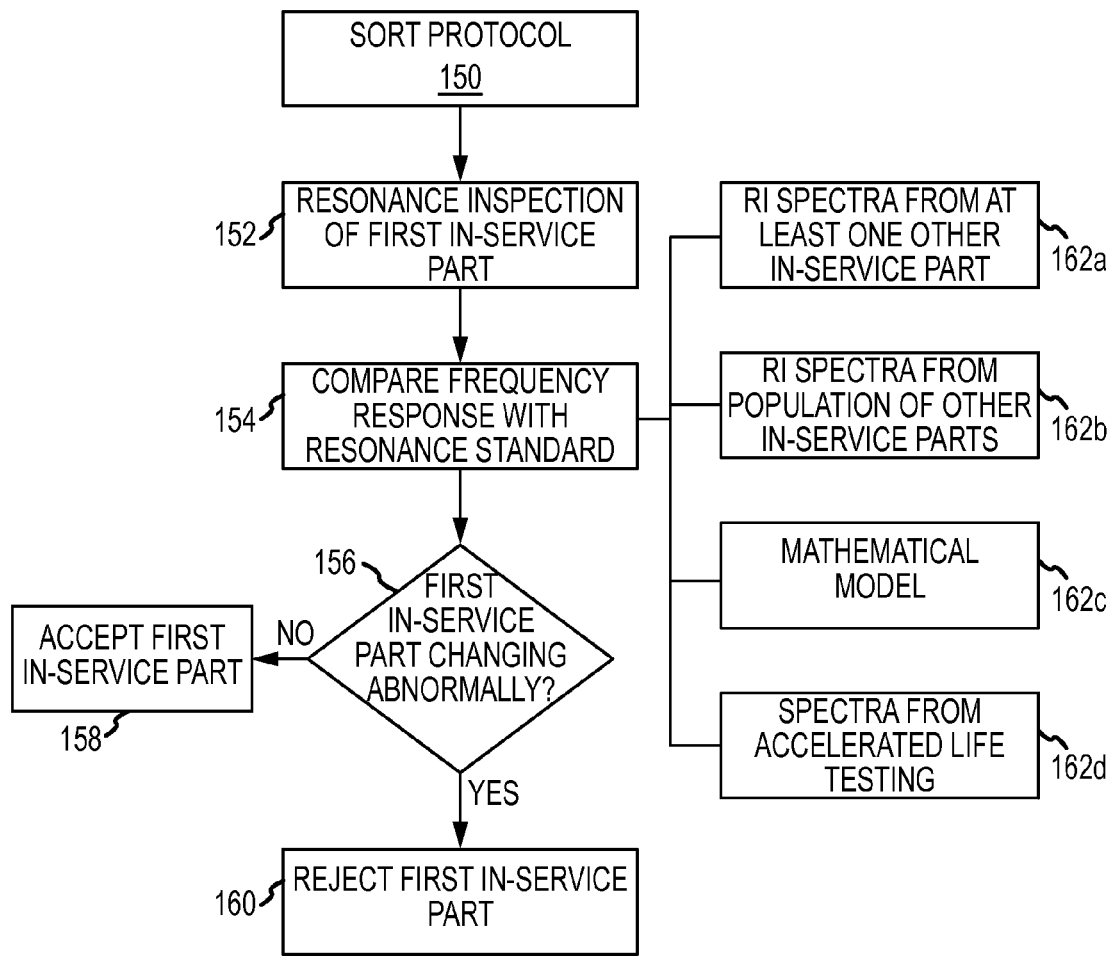
FIG. 6 is one embodiment of an in-service part sort protocol that may be utilized by a resonance inspection tool.

One embodiment of a sort protocol is presented in FIG. 6 and is identified by reference numeral 150. The sort protocol 150 may be utilized by the in-service part sort logic 114 of the resonance inspection tool 100 shown in FIG. 3, and is configured for the assessment of in-service parts. Generally, the sort protocol 150 is directed to determining whether or not an in-service part is experiencing normal changes while in service. Stated another way, the sort protocol 130 may be characterized as being directed to determining whether an in-service part is aging normally or abnormally and via a resonance inspection. Each resonance inspection of an in-service part may be conducted while the in-service part remains in an installed state or condition (e.g., in situ) for purposes of the sort protocol 150. Alternatively, each resonance inspection of an in-service part may be conducted with the in-service part being in an uninstalled state or condition (e.g., after having been removed from an assembly incorporating the same) for purposes of the sort protocol 150.

A resonance inspection of a first in-service part (e.g., part 120 shown in FIG. 3) is conducted pursuant to step 152 of the sort protocol 150 of FIG. 6 (e.g., via execution of the resonance inspection protocol 130 of FIG. 5). The frequency response of the first in-service part is compared with a resonance standard pursuant to step 154. This "resonance standard" may be incorporated by the library 118 used by the resonance inspection tool 100 (FIG. 3) and/or may be utilized by the in-service part sort logic 114, and in any case may characterize or define what should be a "normal change" for a predetermined in-service part (e.g., to determine whether the first in-service part is changing or aging in a normal manner or fashion). That is, the comparison of step 154 is undertaken for purposes of determining whether the first in-service part is changing normally or abnormally (step 156). If the comparison with the resonance standard (step 154) determines that the first in-service part is changing abnormally, the sort protocol 150 proceeds from step 156 to step 160. A first in-service part that is changing abnormally may be rejected by the sort protocol 150 pursuant to step 160 (e.g., the first in-service part may be designated to be taken out of service). A first in-service part that is changing normally is accepted by the sort protocol 150 pursuant to step 158 (e.g., the first in-service part may be returned to service).

The resonance standard associated with step 154 may include actual and/or projected/predicted resonance inspection results. Moreover, these resonance inspection results may be from various points in time over the life cycle of a part (e.g., resonance inspection results when in the form of a new production part, resonance inspection results at or associated with 5,000 cycles of usage, resonance inspection results at or associated with 10,000 cycles of usage, resonance inspection results at or associated with 15,000 cycles of usage, and so forth). Step 156 of the sort protocol 150 may or may not take usage data (e.g., hours or cycles of operation) into account when assessing a particular in-service part. For instance, step 156 could be configured so that resonance inspection results from the in-service part being assessed via the sort protocol 150 would have to "match" data in the resonance standard having the same or comparable usage data (e.g., if the in-service part that was being assessed via the sort protocol 150 was at 10,000 cycles of usage, step 156 could be configured such that resonance inspection results from this in-service part would have to match data in the resonance standard that are also associated with 10,000 cycles of usage). Step 156 could also be configured so that resonance inspection results from the in-service part being assessed via the sort protocol 150 would only need to "match" data in the resonance standard, regardless of any associated usage data (e.g., step 156 could be configured to determine that a part at 10,000 cycles was changing normally, even though its resonance inspection results "matched" data in the resonance standard that was in fact associated with 20,000 cycles).

The resonance standard associated with step 154 of the sort protocol 150 of FIG. 6 may be of various forms. Representative resonance standards are shown in FIG. 6. The resonance standard for step 154 may be in the form of: 1) spectra from one or more other in-service parts (e.g., spectra from a resonance inspection previously conducted on one or more in-service parts other than that being inspected pursuant to the sort protocol 150 (box 162*a*); 2) one or more spectra from a population of other in-service parts (box 162*b*); 3) resonance inspection results predicted and/or derived via mathematical modeling (box 162*c*); and 4) spectra obtained from accelerated life testing (box 162*d*).

The resonance standard associated with step 154 of the sort protocol 150 could be in the form of any one or more of the type of spectra 124 shown in FIG. 4 (e.g., box 162*a*). If the resonance inspection results from the resonance inspection conducted pursuant to step 152 matched or complied with any of these spectra 124 in one or more respects, the in-service part could be accepted by step 158 of the sort protocol 150.

The resonance standard used by step 154 of the sort protocol 150 may be based upon a population of in-service parts (box 162*b*). This population of in-service parts does not need to include the first in-service part that is being assessed by the sort protocol 150. The population of in-service parts may be viewed as a "peer group" for purposes of assessing the first in-service part via the sort protocol 150 (e.g., other parts manufactured in accordance with common specifications and/or that are functionally interchangeable with the first in-service part). For instance, the resonance standard may be in the form of spectra (e.g., spectra 124 from FIG. 4) from each of a plurality of in-service parts that are within the population. If the comparison of step 154 determines that the resonance inspection results from the first in-service part (step 152) match or comply with any of these spectra from the population in one or more respects, the first in-service part may be accepted pursuant to step 158 of the sort protocol 150. The resonance standard associated with step 154 may also be in the form of an average of spectra from each of a plurality of in-service parts that are within the noted population. If the comparison of step 154 determines that the resonance inspection results (step 152) match or comply with this spectral average from the population in one or more respects, the first in-service part may be accepted pursuant to step 158 of the sort protocol 150.

The resonance standard associated with step 154 of the sort protocol 150 may also be provided by mathematical modeling (box 162*c*). This mathematical modeling may be used to generate resonance inspection results for various times over the life of a part that is changing normally. If the comparison of step 154 determines that the resonance inspection results (step 152) match or comply with any of these mathematically derived resonance inspection results in one or more respects, the first in-service part may be accepted pursuant to step 158 of the sort protocol 150.

The resonance standard associated with step 154 of the sort protocol 150 may also be provided by accelerated life testing (box 162*d*). Resonance inspection results may be acquired as a part undergoes accelerated life testing, and these resonance inspection results may be used by the resonance standard associated with step 154. If the comparison of step 154 determines that the resonance inspection results (step 152) match or comply with any of the resonance inspection results acquired during the accelerated life testing in one or more respects, the first in-service part may be accepted pursuant to step 158 of the sort protocol 150.

Figure 7:
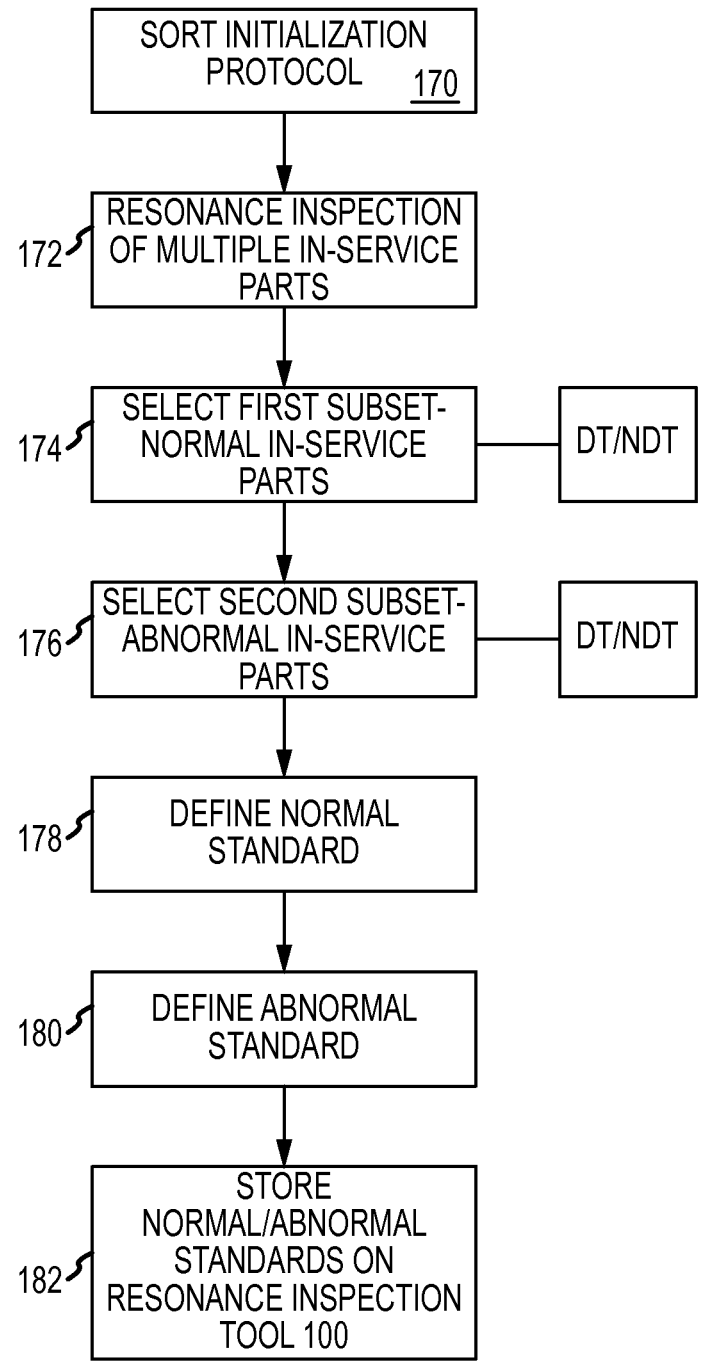
FIG. 7 is one embodiment of an in-service part sort initialization protocol that may be utilized by a resonance inspection tool.

One embodiment of a sort initialization protocol is presented in FIG. 7 and is identified by reference numeral 170. The sort initialization protocol 170 may be utilized by and/or to configure the in-service part sort logic 114 of the resonance inspection tool 100 shown in FIG. 3, and is thereby associated with the assessment of in-service parts (e.g., logic configured to determine whether an in-service part should be rejected or accepted). A resonance inspection of a plurality of in-service parts (e.g., part 120 shown in FIG. 3) is conducted pursuant to step 172 of the sort initialization protocol 170 of FIG. 7 (e.g., via execution of the resonance inspection protocol 130 of FIG. 5). A first subset of "normal" in-service parts (that underwent resonance inspection pursuant to step 172) is defined pursuant to step 174. A determination as to whether or not a given in-service part from step 172 is "normal" for purposes of step 174 may be undertaken in any appropriate manner, for instance using destructive testing, nondestructive testing, and/or a combination thereof.

A second subset of "abnormal" in-service parts (that underwent resonance inspection pursuant to step 172) is defined pursuant to step 176 of the sort initialization protocol 170. A determination as to whether or not a given in-service part from step 172 is "abnormal" for purposes of step 176 may be undertaken in any appropriate manner, for instance using destructive testing, nondestructive testing, or a combination thereof. In one embodiment, an in-service part that undergoes a resonance inspection pursuant to step 172 is characterized as normal (step 174) or abnormal (step 176) other than by the results of the resonance inspection associated with step 172 (e.g., via DT and/or NDT).

One or more destructive testing techniques may be used, one or more nondestructive testing techniques may be used, or both, in relation to each of steps 174 and 176 of the sort initialization protocol 170 of FIG. 7. Representative nondestructive testing techniques that may be used in relation to each of steps 174 and 176 includes without limitation visual inspection, microscopy, magnetic particle, penetrant, eddy current, x-ray, computed tomography, flash thermography, ultrasound, sonic infra-red, phased array, or the like. Representative destructive testing techniques that may be used in relation to each of steps 174 and 176 includes without limitation fatigue testing, static testing, thermal testing, metalography, sectioning, ablation, chemical reduction, or the like.

Step 178 of the sort initialization protocol 170 of FIG. 7 is directed to defining a normal standard, while step 180 of the protocol 170 is directed to defining an abnormal standard. The normal standard associated with step 178 may be defined by one or more of the in-service parts associated with step 174 and may utilize results of the corresponding resonance inspection from step 172 (e.g., spectra of each in-service part within the first subset could be used by the normal standard; an average spectra from a plurality of in-service parts within the first subset could be used by the normal standard). Similarly, the abnormal standard associated with step 180 may be defined by one or more of the in-service parts associated with step 176 and may utilize results of the corresponding resonance inspection from step 172 (e.g., spectra of each in-service part within the second subset could be used by the abnormal standard; an average spectra from a plurality of in-service parts within the second subset could be used by the abnormal standard). Both the normal standard (178) and the abnormal standard (step 180) may be stored (e.g., on a computer-readable storage medium) for use by the resonance inspection tool 100 through execution of step 182 of the sort initialization protocol 170 (e.g., included in the library 118 shown in FIG. 3).

Figure 8:
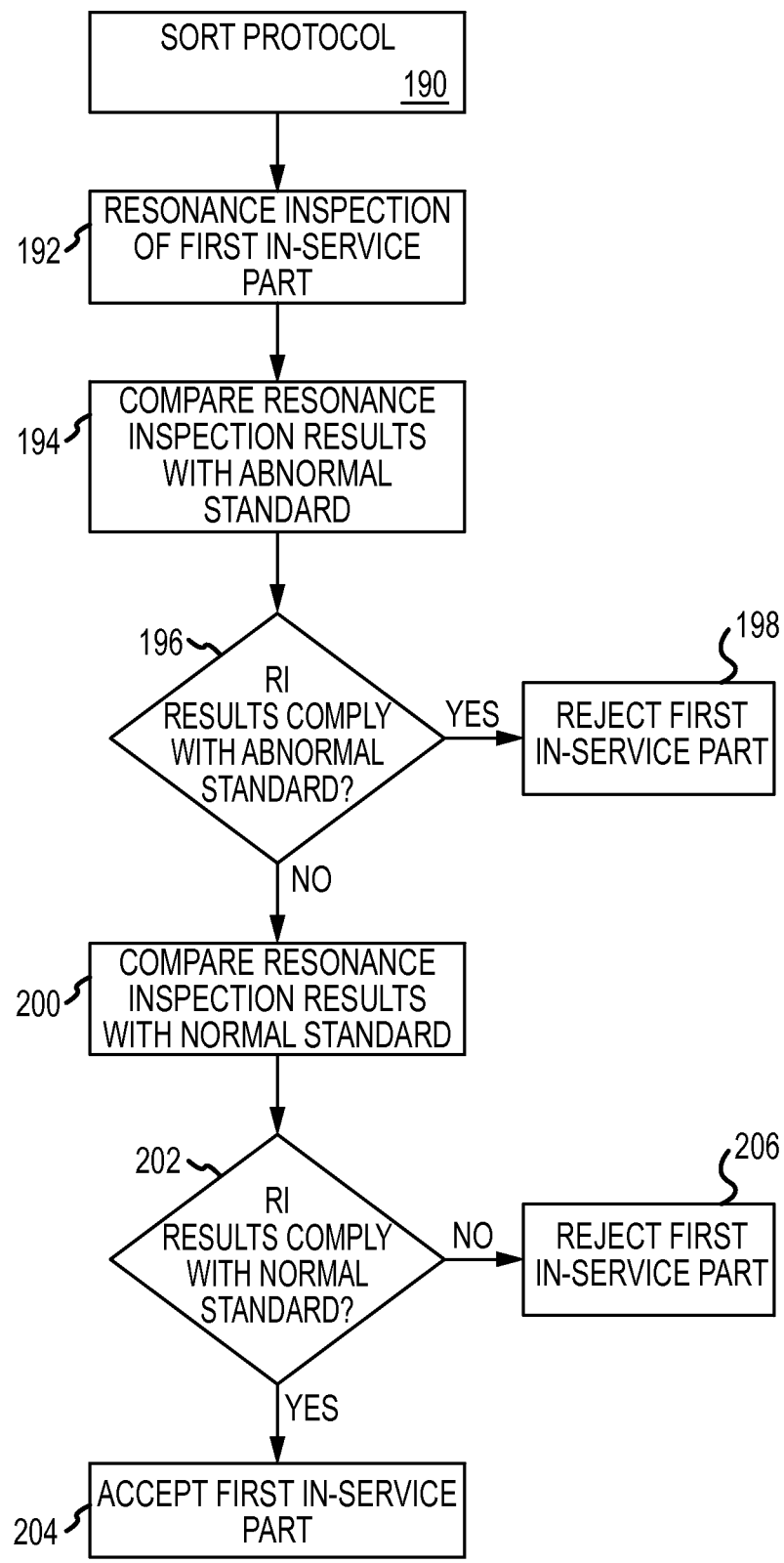
FIG. 8 is one embodiment of an in-service part sort protocol that may be utilized by a resonance inspection tool, including in conjunction with the sort initialization protocol of FIG. 7.

Another embodiment of a sort protocol is presented in FIG. 8 and is identified by reference numeral 190. The sort protocol 190 may be utilized by the in-service part sort logic 114 of the resonance inspection tool 100 shown in FIG. 3, and is configured for the assessment of in-service parts. The resonance inspection of an in-service part may be conducted while the in-service part remains in an installed state or condition (e.g., in situ) for purposes of the sort protocol 190. Alternatively, the resonance inspection of an in-service part may be conducted with the in-service part being in an uninstalled state or condition (e.g., after having been removed from an assembly incorporating the same) for purposes of the sort protocol 190.

A resonance inspection of a first in-service part (e.g., part 120 shown in FIG. 3) is conducted pursuant to step 192 of the sort protocol 190 of FIG. 8 (e.g., via execution of the resonance inspection protocol 130 of FIG. 5). Results of the resonance inspection from step 192 may be compared with an abnormal standard (step 194). The abnormal standard associated with steps 194 and 196 may be provided by the sort initialization protocol 170 of FIG. 7. In any case, step 196 of the sort protocol 190 is directed to determining if resonance inspection results (step 192) comply with the abnormal standard. The first in-service part is rejected if the resonance inspection results (step 192) do in fact comply with the abnormal standard (step 198).

Results of the resonance inspection may be compared with a normal standard (step 200). Step 202 is directed to determining if resonance inspection results (step 192) comply with the normal standard. The normal standard associated with steps 200 and 202 may be provided by the sort initialization protocol 170 of FIG. 7. In any case, the first in-service part is accepted if resonance inspection results (step 192) do in fact comply with the normal standard (step 204). The first in-service part is rejected if resonance inspection results (step 192) do not comply with the normal standard (step 206) in the illustrated embodiment.

The protocol 190 may be configured to execute steps 194 and 200 in an order different from that shown in FIG. 8. Consider the case where the protocol 190 is configured to execute step 200 (comparison with a normal standard) before step 194 (comparison with an abnormal standard). If through execution of step 202 a determination is made that resonance inspection results (step 192) do in fact comply with the normal standard, steps 194 and 196 could then be executed. If through execution of step 196 a determination is made that resonance inspection results (step 192) do not comply with the abnormal standard, the protocol 190 could then proceed to the execution of step 204 (where the first in-service part is accepted by the resonance inspection tool 100). However, if a determination was made that the resonance inspection results (step 192) comply with the abnormal standard pursuant to step 196, steps 202 and 196 of the protocol 190 would be providing inconsistent results. In this case, the sort protocol 190 could be configured to reject the first in-service part (step 198)—even through resonance inspection results of the first in-service part were determined by the resonance inspection tool 100 to comply with the normal standard (step 202).

The sort protocol 190 could also be configured to address a condition when resonance inspection results from step 194 do no match either the normal standard (step 200) or the abnormal standard (step 196). One option would be to associate the first in-service part with an unknown condition, and to thereafter further assess the first in-service part. The results of this further analysis could be used to update either the abnormal standard or the normal standard, depending upon whether the first in-service part was determined to be normal or abnormal.

Figure 9:
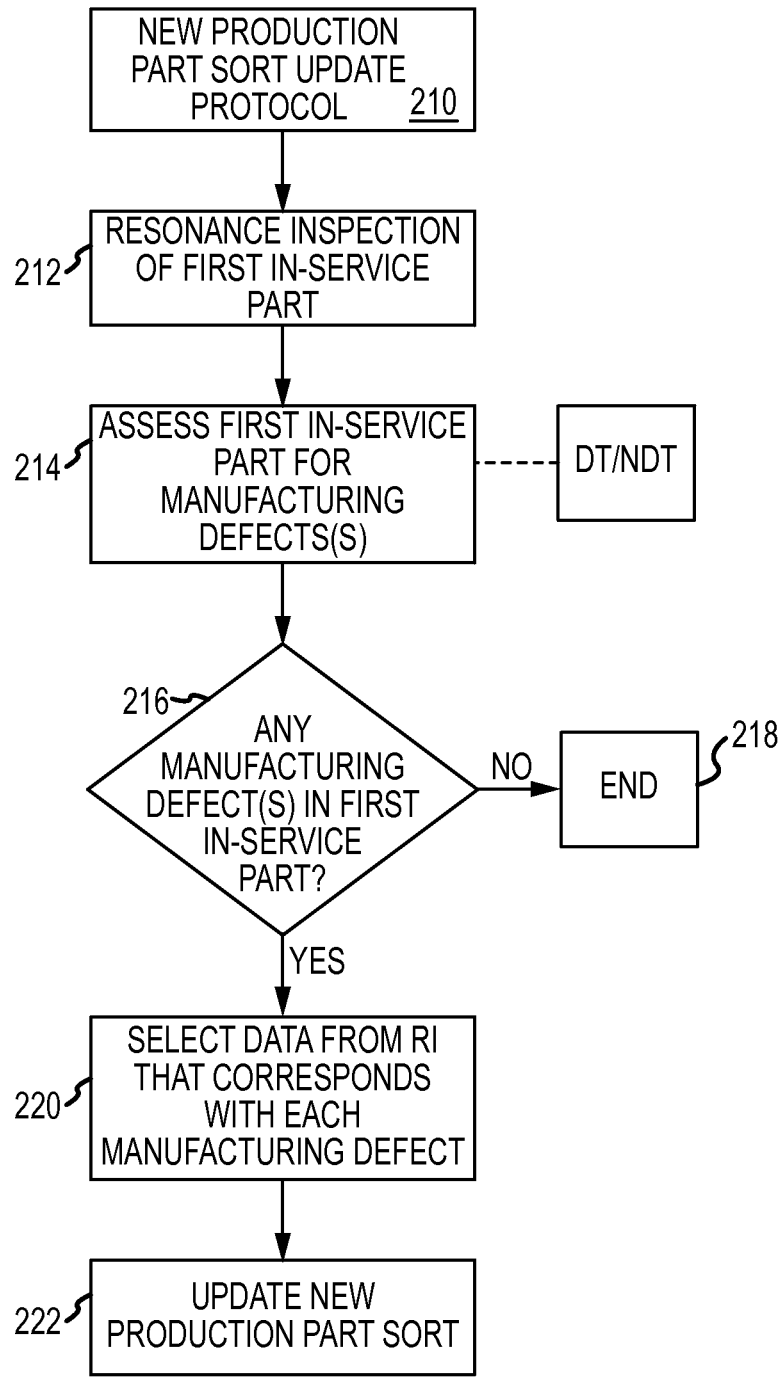
FIG. 9 is one embodiment of a new production part sort update protocol that may be utilized by a resonance inspection tool.

One embodiment of a new production part sort update protocol is presented in FIG. 9 and is identified by reference numeral 210. The sort update protocol 210 may be utilized by the new production part sort logic 112 of the resonance inspection tool 100 shown in FIG. 3. Generally, the sort update protocol 210 of FIG. 9 is configured to assess one or more in-service parts, and utilizes this assessment for purposes of updating the new production part sort logic 112 of the resonance inspection tool 100. The resonance inspection of an in-service part may be conducted while the in-service part remains in an installed state or condition (e.g., in situ) for purposes of the sort update protocol 210. Alternatively, the resonance inspection of an in-service part may be conducted with the in-service part being in an uninstalled state or condition (e.g., after having been removed from an assembly incorporating the same) for purposes of the sort update protocol 210.

A resonance inspection of a first in-service part (e.g., part 120 shown in FIG. 3) is conducted pursuant to step 212 of the sort update protocol 210 of FIG. 9 (e.g., via execution of the resonance inspection protocol 130 of FIG. 5). The first in-service part is assessed for any manufacturing defects pursuant to step 214 of the sort update protocol 210. Any appropriate technique or combination of techniques may be used to determine whether or not the first in-service part has one or more manufacturing defects (e.g., via destructive testing and/or nondestructive testing). If no manufacturing defects are identified in the first in-service part, the sort update protocol proceeds from step 216 to step 218, which terminates the protocol 210. However, if at least one manufacturing defect is identified in the first in-service part (through execution of step 214), the sort update protocol 210 proceeds from step 216 to step 220. Pursuant to step 220, data from the resonance inspection (step 212) that corresponds with a given manufacturing defect is selected. This may be done in relation to each manufacturing defect that is identified in the first in-service part through execution of step 214. The data from the resonance inspection that corresponds with a manufacturing defect may then be used to update the new production part sort logic 112 for the resonance inspection tool 100 of FIG. 3 (step 222). For instance, the library 118 of the resonance inspection tool 100 may be updated such that new production parts that originally would have been accepted by the resonance inspection tool 100 (prior to execution of the sort update protocol 210) will now be rejected by the resonance inspection tool 100 if any such new production part includes a manufacturing defect that has been identified through execution of the sort update protocol 210 of FIG. 9.

Figure 10:
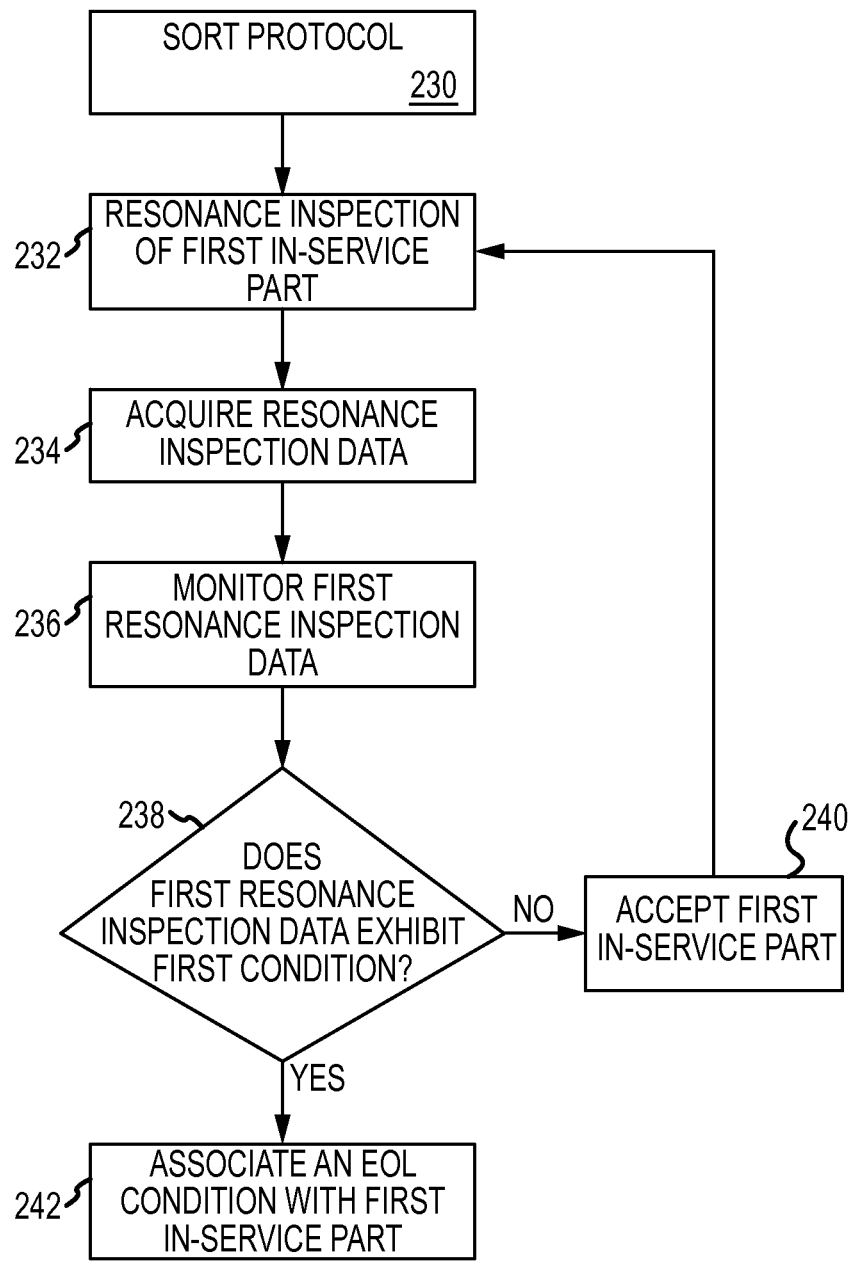
FIG. 10 is another embodiment of an in-service part sort protocol that may be utilized by a resonance inspection tool.

Another embodiment of a sort protocol is presented in FIG. 10 and is identified by reference numeral 230. The sort protocol 230 may be utilized by the in-service part sort logic 114 of the resonance inspection tool 100 shown in FIG. 3, and is configured for the assessment of in-service parts. The resonance inspection of an in-service part may be conducted while the in-service part remains in an installed state or condition (e.g., in situ) for purposes of the sort protocol 230. Alternatively, the resonance inspection of an in-service part may be conducted with the in-service part being in an uninstalled state or condition (e.g., after having been removed from an assembly incorporating the same) for purposes of the sort protocol 230.

The sort protocol 230 is generally directed to monitoring in-service parts for an end-of-life ("EOL") state or condition based upon resonance inspections of the in-service part that are conducted over time. Spaced-in-time resonance inspections of an in-service part may be conducted on any appropriate basis. For instance, an in-service part could be scheduled for a resonance inspection based upon time (e.g., on a calendar quarterly basis), based upon usage/usage data (e.g., hours of operation; cycles of operation), or the like. In one embodiment, an in-service part is scheduled for a resonance inspection based upon what may be characterized as a "cycle target." Such a "cycle target" could be in the form of the in-service part being within a range of cycles, having been used for a minimum number of cycles, or the like.

A resonance inspection of a first in-service part (e.g., part 120 shown in FIG. 3) is conducted pursuant to step 232 of the sort protocol 230 of FIG. 10 (e.g., via execution of the resonance inspection protocol 130 of FIG. 5). Resonance inspection data (e.g., the frequency response of the first in-service part) is acquired pursuant to step 234. The acquisition of resonance inspection data from step 234 may be characterized as being part of the resonance inspection associated with step 232.

Step 236 of the sort protocol 230 is directed to the monitoring first resonance inspection data. More specifically, step 236 is directed to monitoring first resonance inspection data for an occurrence of a first condition. This "first condition" may be in the form of a certain time-rate-of-change in the first resonance inspection data, and will be discussed in more detail below. In the event the first resonance inspection data does not exhibit a first condition, the sort protocol 230 proceeds from step 238 to step 240. As the first condition was not identified in the first resonance inspection data, step 240 is directed to accepting the first in-service part. For instance, the protocol 230 may designate the first in-service part as being appropriate for further service. Another resonance inspection of the first in-service part may be conducted at a later time (e.g., after the expiration of a designated number of hours of operation or cycles of operation). As such, step 240 may return control to step 232 of the sort protocol 230 for repetition in accordance with the foregoing. Since a subsequent resonance inspection will typically be conducted at a later point in time, step 240 could also terminate the protocol 230 (e.g., an "end" step, and such that the protocol 230 would be re-run for each resonance inspection of the first in-service part).

In the event the sort protocol 230 identifies an occurrence of a first condition (e.g., via steps 236 and/or 238), the protocol 230 proceeds from step 238 to step 242. Step 242 is directed to associating an "end-of-life" or EOL condition or state with the first in-service part. This may entail designating the first in-service part for retirement such that the first in-service part is not returned to service.

The first resonance inspection data (step 236) may be characterized as being part of and/or embodied by the resonance inspection data (step 234). In one embodiment, the first resonance inspection data (step 236) may be only part and/or may relate to only part of the resonance inspection data (step 234). The first resonance inspection data (step 236) may also be characterized as being based upon and/or derived from the resonance inspection data (step 234).

The first resonance inspection data (step 236) may be in the form of a frequency shift in the resonance inspection data (step 234) over time. The first resonance inspection data (step 236) may be in the form of: 1) a relative shift of at least one peak in the resonance inspection data acquired from multiple resonance inspections of the first in-service part (e.g., a shift of a first peak in the resonance inspection data relative to a second peak in the resonance inspection data); 2) an absolute shift of at least one peak in the resonance inspection data acquired from multiple resonance inspections of the first in-service part (e.g., a shift of a first peak in the resonance inspection data); 3) an appearance of at least one peak in the resonance inspection data acquired from multiple resonance inspections of the first in-service part; and 4) a disappearance of at least one peak in the resonance inspection data acquired from multiple resonance inspections of the first in-service part.

The "first condition" associated with step 238 may be characterized as being directed to a time-rate-of-change in resonance inspection results from resonance inspection to resonance inspection. That is, one or more parameters embodied by and/or relating to the resonance inspection results may be monitored from resonance inspection to resonance inspection to assess any corresponding change that may be occurring in relation to any such parameter. A certain change in any such parameter may be characterized as an occurrence of the first condition (step 238).

Figure 11:
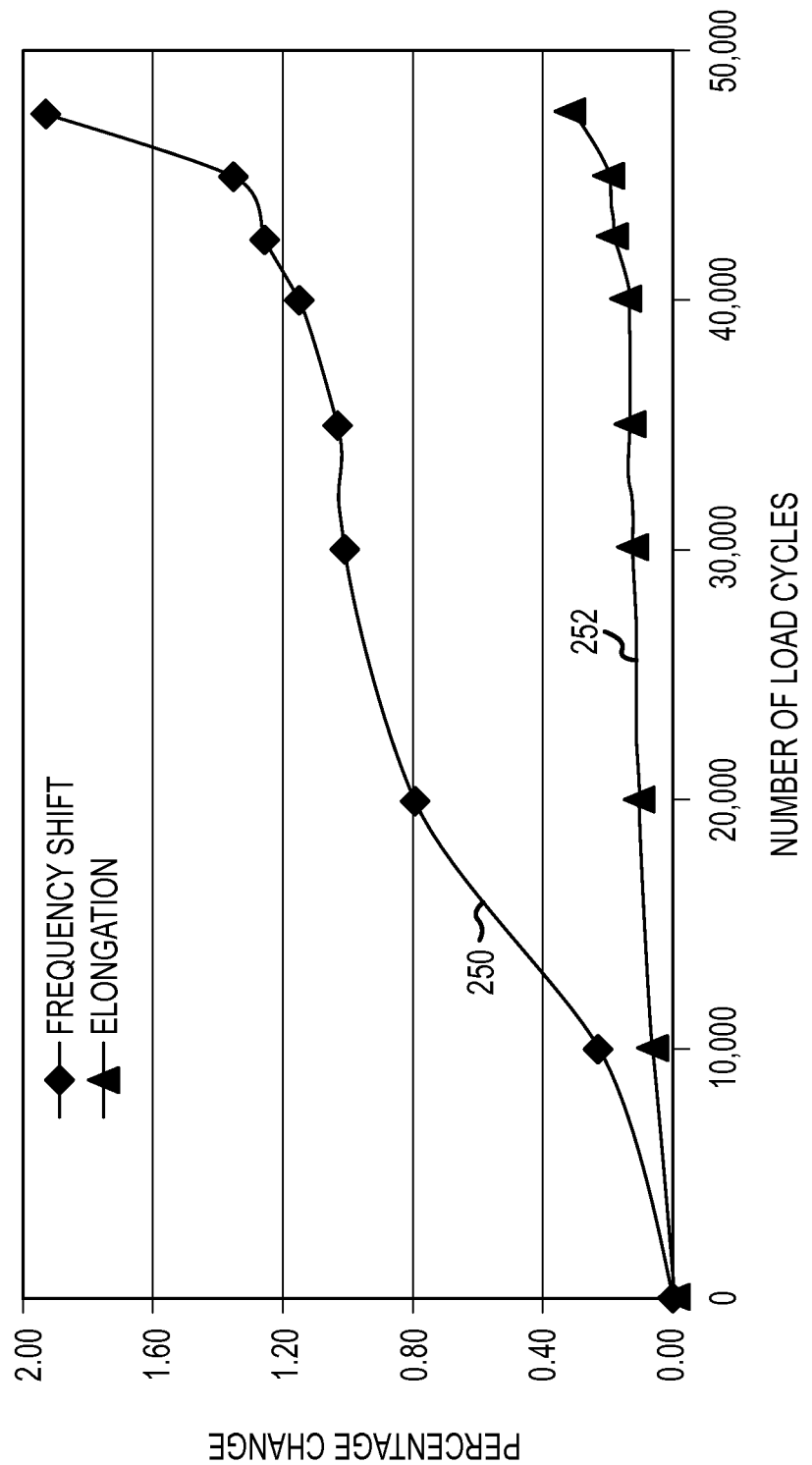
FIG. 11 illustrates a time-rate-of-change of resonance inspection results that may be used by the in-service part sort protocol of FIG. 10.

FIG. 11 illustrates representative first resonance inspection data that may be utilized by the sort protocol 230 of FIG. 10. Plot 250 may be in the form of a frequency shift of a certain peak in the resonance inspection results from resonance inspection to resonance inspection (the "diamonds" being data points obtained from different resonance inspections over time). Plot 252 may be in the form of an "elongation" between a pair of peaks in the resonance inspection results from resonance inspection to resonance inspection (the "triangles" being data points obtained from different resonance inspections over time). "Elongation" means that the spacing between a pair of peaks in the resonance inspection results is being monitored for increases.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method of evaluating new production parts, wherein a resonance inspection comprises exciting a part at a plurality of input frequencies and obtaining a frequency response of the part at said plurality of input frequencies, wherein said method comprises the steps of:
    performing said resonance inspection on a first new production part using a new production part sort functionality of a resonance inspection tool;
    performing said resonance inspection on a first in-service part after said resonance inspection has been performed on said first new production part;
    identifying a first manufacturing defect in said first in-service part;
    selecting resonance inspection data from said resonance inspection on said first in-service part that corresponds with said first manufacturing defect and that defines selected resonance inspection data;
    generating an updated new production part sort functionality of said resonance inspection tool based upon said selected resonance inspection data, wherein said updated new production part sort functionality is adjusted based upon said selected resonance inspection data from said resonance inspection of said first in-service part and where said selected resonance inspection data corresponds with said first manufacturing defect; and
    performing said resonance inspection on a second new production part, wherein said resonance inspection of said second new production part uses said updated new production part sort functionality of said resonance inspection tool after said generating step, wherein said first and second new production parts are in a common part class, and wherein said first in-service part is in a different part class from said common part class of said first and second new production parts.

2. The method of claim 1, wherein said resonance inspection in relation to said first in-service part comprises using at least one transducer that excites said first in-service part through a range of frequencies and thereafter using at least two other transducers to measure said frequency response of said first in-service part.

3. The method of claim 1, wherein said resonance inspection of said first in-service part comprises using a first transducer that excites said first in-service part at each of multiple frequencies and also using said first transducer to measure said frequency response of said first in-service part.

4. The method of claim 1, wherein said resonance inspection of said first in-service part is performed with said first in-service part being in an installed condition.

5. The method of claim 1, wherein said resonance inspection of said first in-service part is performed with said first in-service part being in an uninstalled condition.

6. The method of claim 1, wherein said identifying a first manufacturing defect step uses data other than results from said resonance inspection of said first in-service part.

7. The method of claim 1, wherein said identifying a first manufacturing defect step comprises testing selected from the group consisting of destructive testing, nondestructive testing, and any combination thereof.

8. The method of claim 1, wherein prior to said generating step, said new production sort functionality of said resonance inspection tool was configured to accept a part having said first manufacturing defect.

9. The method of claim 8, wherein after said generating step, said updated new production sort functionality of said resonance inspection tool is configured to reject a part having said first manufacturing defect.

10. The method of claim 1, wherein said first new production part comprises said first manufacturing defect, and wherein said new production part sort functionality accepts said first new production part and which occurs prior to said generating step.

11. The method of claim 10, wherein said second new production part comprises said first manufacturing defect, and wherein said updated new production part sort functionality rejects said second new production part and which occurs after said generating step.

12. The method of claim 1, wherein said first and second new production parts are in a new production part class, wherein said first in-service part is in an in-service part class that is different from said new production part class, wherein said new production part class is for parts that have not yet been released from production, and wherein said in-service part class is for parts that have been released from production.

* * * * *